US010378069B2

(12) United States Patent
Frankel et al.

(10) Patent No.: US 10,378,069 B2
(45) Date of Patent: Aug. 13, 2019

(54) COMPOSITIONS AND METHODS FOR DETECTING ZIKA VIRUS

(71) Applicant: Abbott Molecular Inc., Des Plaines, IL (US)

(72) Inventors: Matthew Frankel, Abbott Park, IL (US); George Schneider, Abbott Park, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 15/633,449

(22) Filed: Jun. 26, 2017

(65) Prior Publication Data

US 2017/0369931 A1  Dec. 28, 2017

Related U.S. Application Data

(60) Provisional application No. 62/355,260, filed on Jun. 27, 2016.

(51) Int. Cl.
| | | |
|---|---|---|
| C12Q 1/689 | (2018.01) | |
| C12Q 1/6806 | (2018.01) | |
| C12N 15/10 | (2006.01) | |
| C12Q 1/6893 | (2018.01) | |
| C12Q 1/70 | (2006.01) | |

(52) U.S. Cl.
CPC ......... *C12Q 1/689* (2013.01); *C12N 15/1003* (2013.01); *C12Q 1/6806* (2013.01); *C12Q 1/6893* (2013.01); *C12Q 1/701* (2013.01); *C12Q 2600/118* (2013.01); *C12Q 2600/166* (2013.01)

(58) Field of Classification Search
CPC .................................................. C12N 15/1003
See application file for complete search history.

(56) References Cited

U.S. PATENT DOCUMENTS

| 5,118,801 A | 6/1992 | Lizardi et al. |
| 5,312,728 A | 5/1994 | Lizardi et al. |

FOREIGN PATENT DOCUMENTS

| CN | 105506188 | 4/2016 |

OTHER PUBLICATIONS

Altschul et al., "Basic local alignment search tool," J. Molecular Biol., 1990, 215(3): 403-410.
Altschul et al., "Gapped BLAST and PSI-BLAST: a new generation of protein database search programs," Nucleic Acids Res., 25(17): 3389-3402 (1997).
Ausubel et al., Current Protocols in Molecular Biology, John Wiley & Sons, New York (2016).

Balm et al., "A diagnostic polymerase chain reaction assay for Zika virus," Journal of Medical Virology, 2012, vol. 84, No. 9, pp. 1501-1505.
Beigert et al., "Sequence context-specific profiles for homology searching," Proc. Nail. Acad. Sci. USA, 2009, 106(10): 3770-3775.
Cao-Lormeau et al., "Guillain-Barré Syndrome outbreak associated with Zika virus infection in French Polynesia: a case-control study," Lancet, 2016, 387:1531-1539.
Cauchemez et al., "Association between Zika virus and microcephaly in French Polynesia, 2013-15: a retrospective study," Lancet, 2016, 387: 2125-2132.
Chan et al., "Zika fever and congenital Zika syndrome: An unexpected emerging arboviral disease," J Infect, 2016, 72:507-524.
Durbin et al., eds., Biological Sequence Analysis: Probalistic Models of Proteins and Nucleic Acids, Cambridge University Press, Cambridge, UK (2009).
Espelund et al., "A simple method for generating single-stranded DNA probes labeled to high activities," Nuc. Acids. Res., 1990, 18(20): 6157-6158.
Faye et al., "One-step RT-PCR for detection of Zika virus," Journal of Clinical Virology, 2008, vol. 43, No. 1, pp. 96-101.
Faye et al., "Quantitative real-time PCR detection of Zika virus and evaluation with field-caught Mosquitoes," Virology Journal, 2013, vol. 10, No. 1, p. 311.
Freeman et al., "Quantitative RT-PCR: pitfalls and potential," Biotechniques, 1999, 26(1): 112-125.
Genbank Accession No. AY632535 (2010).
Genbank Accession No. EU545988 (2008).
Genbank Accession No. HQ234499 (2012).
Genbank Accession No. HQ234500.1 (2012).
Genbank Accession No. HQ234501 (2012).
Genbank Accession No. KU955593 (2016).
Gusfield, Algorithms on Strings, Trees and Sequences, Cambridge University Press, Cambridge UK (1997).
Haddow et al., "Genetic Characterization of Zika Virus Strains: Geographic Expansion of the Asian Lineage," PLoS Negl Trop Dis, 2012, 6:e1477.
International Search Report and Written Opinion for Application No. PCT/US2017/039275 dated Aug. 30, 2017 (16 pages).
Invitation to Pay Additional Fees for Application No. PCT/US2017/039275 dated Aug. 30, 2017 (16 pages).
Joyce, C., "Quantitative RT-PCR. A review of current methodologies," Methods Mol. Biol., 2002, 193: 83-92.
Lanciotti et al., "Genetic and Serologic Properties of Zika Virus Associated with an Epidemic, Yap State, Micronesia, 2007," Emerging Infectious Diseases, 2008, vol. 14, No. 8, pp. 1232-1239.
Lanciotti et al., "Phylogeny of Zika Virus in Western Hemisphere, 2015," Emerg Infect Dis, 2016, 22:933-935.
Musso et al., "Potential for Zika virus transmission through blood transfusion demonstrated during an outbreak in French Polynesia, Nov. 2013 to Feb. 2014," Euro Surveill, 2014, 19:20761.
Mosso et al., "Potential sexual transmission of Zika virus," Emerg Infect Dis, 2015, 21:359-361.

(Continued)

*Primary Examiner* — Bao Q Li
(74) *Attorney, Agent, or Firm* — Casimir Jones, S.C.; Melissa E. Kolom

(57) ABSTRACT

The invention is directed to compositions, kits, and methods for amplifying and detecting a Zika virus nucleic acid sequence in a sample, which comprises a variety of combinations of forward oligonucleotide primers, reverse oligonucleotide primers, and oligonucleotide probes.

10 Claims, 3 Drawing Sheets

Specification includes a Sequence Listing.

(56) References Cited

OTHER PUBLICATIONS

O'Connell, J. (ed.), RT-PCR Protocols, 1st Ed., Springer-Verlag, New York, NY (2010).

Oliveira et al, "Zika virus intrauterine infection causes fetal brain abnormality and microcephaly: tip of the iceberg?," Ultrasound Obstet Gynecol, 2016, 47:6-7.

Sambrook et al., Molecular Cloning. A Laboratory Manual, 4th ed., Cold Spring Harbor Press, Cold Spring Harbor, New York (2012).

Schuler-Faccini et al., "Possible Association Between Zika Virus Infection and Microcephaly—Brazil, 2015," MMWR Morb Mortal Wkly Rep 2016, 65:59-62.

Shu et al., Phylogenetic analysis revealed the central roles of two African countries in the evolution and worldwide spread of Zika virus, Virologica Sinica, 2016, vol. 31, No. 2, pp. 118-130.

Söding, "Protein homology detectionby HMM-HMM comparison," Bioinformatics, 2005, 21(7): 951-960.

Tang et al., "Simple and effective method for generating single-stranded DNA targets and probes," Biotechniques, 2006, 40(6): 759-763.

Van den Berg et al., "Guillain-Barré-syndroom na zikavirus-infectie," Ned Tijdschr Geneeskdi, 160: D155 (2016).

Ye et a., "Genomatic characterization and phylogenetic analysis of Zika virus circulating in the Americas," Infection, Genetics and Evolution, 2016, vol. 43, pp. 43-49.

Faye et al., "Molecular Evolution of Zika Virus during Its Emergence in the 20th Century," PLOS Neglected Tropical Diseases, 2014, vol. 8, No. 1, p. e2636.

International Search Report and Written Opinion for Application No. PCT/US2017/039275 dated Nov. 17, 2017 (20 pages).

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gaaccagatg acgtcgattg                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gaaccagatg atgtcgattg                                                  20

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
caggttccgt acacaaccca agt                                              23

<210> SEQ ID NO 4
<211> LENGTH: 17
<212> TYPE: DNA
<213> ORGANISM: Artificial Sequence
<220> FEATURE:
<223> OTHER INFORMATION: Synthetic

<400> SEQUENCE: 4
tggtgcaaca cgacatc                                                     17

<210> SEQ ID NO 5
<211> LENGTH: 17
<212> TYPE: DNA
<213> ORGANISM: Artificial Sequence
<220> FEATURE:
<223> OTHER INFORMATION: Synthetic

<400> SEQUENCE: 5
tggtgcaaca cgacgtc                                                     17

<210> SEQ ID NO 6
<211> LENGTH: 21
<212> TYPE: DNA
<213> ORGANISM: Artificial Sequence
<220> FEATURE:
```

<223> OTHER INFORMATION: Synthetic

<400> SEQUENCE: 6
ggcaggaacc ctaagaaacc t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggcaggaacc ctaacaaacc t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
ggcaggaatc ccaacaaacc t                                              21

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
ctatgaggcc atcctggagg ta                                             22

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ctatgaggcc atcttggagg ta                                             22

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tggcttgaag caagaatgct                                                20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
ggatgggaga tccattgtgg t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggatggtaga tccattgtgg t                                              21

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
ctcccggatg ctccatcc                                                  18

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccaccaagat gaactgattg                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ccaccaagat gaattgattg                                                20

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
gcctcatcaa cagatggggt tc                                             22

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
gtggggaaaa aagaggctat gga                                            23

<210> SEQ ID NO 19
<211> LENGTH: 26
<212> TYPE: DNA
<213> ORGANISM: Artificial Sequence
<220> FEATURE:
<223> OTHER INFORMATION: Synthetic

```
<400> SEQUENCE: 19
ctcttcctct ccttcctagc attgat                                            26

<210> SEQ ID NO 20
<211> LENGTH: 17
<212> TYPE: DNA
<213> ORGANISM: Artificial Sequence
<220> FEATURE:
<223> OTHER INFORMATION: Synthetic

<400> SEQUENCE: 20
gctgccatgt tgagaat                                                      17

<210> SEQ ID NO 21
<211> LENGTH: 62
<212> TYPE: DNA
<213> ORGANISM: Zika virus

<400> SEQUENCE: 21
gaaccagatg atgtcgattg ctggtgcaac acgacatcaa cttgggttgt gtacggaacc       60
tg                                                                      62

<210> SEQ ID NO 22
<211> LENGTH: 134
<212> TYPE: DNA
<213> ORGANISM: Zika virus

<400> SEQUENCE: 22
ggcaggaacc ctaacaaacc tggagatgag tacatgtatg gaggtggatg tgcagagacc       60
gatgaagacc atgcacactg gcttgaagca agaatgcttc ttgacaacat ctacctccag      120
gatggcctca tagc                                                        134

<210> SEQ ID NO 23
<211> LENGTH: 94
<212> TYPE: DNA
<213> ORGANISM: Zika virus

<400> SEQUENCE: 23
ggatggtaga tccattgtgg tcccttgccg ccaccaagat gaattgattg gccgagcccg       60
tgtatcacca ggggcaggat ggagcatccg ggag                                   94

<210> SEQ ID NO 24
<211> LENGTH: 118
<212> TYPE: DNA
<213> ORGANISM: Zika virus

<400> SEQUENCE: 24
gcctcatcaa cagatggggt tcagtgggga aaaaagaggc tatggaaata ataaagaagt       60
ttaagaaaga tcttgctgcc atgttgagaa taatcaatgc taggaaggag aggaagag        118

<210> SEQ ID NO 25
<211> LENGTH: 17
<212> TYPE: DNA
<213> ORGANISM: Artificial Sequence
<220> FEATURE:
<223> OTHER INFORMATION: Propyne Zika probe 658-2b

<400> SEQUENCE: 25
tggugcaaca cgacgtc                                                      17
```

COMPOSITIONS AND METHODS FOR DETECTING ZIKA VIRUS

CROSS-REFERENCE TO RELATED APPLICATIONS

This application claims priority to U.S. Provisional Patent Application No. 62/355,260, filed Jun. 27, 2016, which is fully incorporated herein by reference.

BRIEF DESCRIPTION OF THE INVENTION

This invention relates to an assay for amplifying and detecting Zika virus nucleic acid sequences in a sample.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,096 Byte ASCII (Text) file named "12866USO1_ST25.txt," created on Jun. 26, 2017.

BACKGROUND OF THE INVENTION

Prior to 2015, Zika virus (ZIKV) was suspected of causing little more than an asymptomatic illness termed Zika fever (also known as Zika virus disease), sometimes characterized by fever, red eyes, joint pain, headache, and a rash that resolved within seven days. The virus was first discovered in 1947 and named after the Zika forest in Uganda, although the first human case was not reported until 1952. The virus is primarily transmitted to humans following a bite by an infected mosquito of the *Aedes* genus, most commonly by the mosquito species *A. Aegypti* and *A. Albopictus*, which are primarily found in tropical and subtropical zones throughout the world. Since it was discovered in 1947, ZIKV has spread beyond Uganda and across Africa, and by the early 1980s the virus had reached Asia; however given the mild nature of the disease, only 14 cases of ZIKV infection were reported prior to 2007.

ZIKV began to attract global attention in 2013, when outbreaks were reported in four groups of Pacific islands: French Polynesia, Easter Island, the Cook Islands, and New Caledonia. Retrospective investigations of these outbreaks indicated a possible association between ZIKV infection in pregnant women and congenital malformations in newborns (Cauchemez et al., *Lancet*, 387:2125-2132 (2016)), including severe neurological and autoimmune complications. The virus was also found in semen (Musso et al., *Emerg Infect Dis*, 21:359-361 (2015)), and in blood donations from asymptomatic donors (Musso et al., *Euro Surveill*, 19:20761 (2014), Chan et al., *J Infect*, 72:507-524 (2016)), suggesting that the virus could be transmitted through sexual contact and blood transfusions.

In March 2015, an outbreak of ZIKV was reported in Brazil; nearly 7000 cases were documented between February and April of that year, which represented the first documented report of locally-acquired ZIKV in the Americas. The virus has continued to spread throughout South America, Central America, and the Caribbean islands. Although still characterized as a mild disease, in October 2015, Brazil noticed an alarming increase in the number of cases of microcephaly since August 2015. Microcephaly is a medical condition in which the brain of a developing fetus does not form properly, resulting in a smaller than normal head, and often long-term mental and developmental disabilities. By November 2015, Brazil declared a national public health emergency as the number of suspected microcephaly cases continued to rise. A January 2016 study conducted by health officials in Brazil and the United States Centers for Disease Control and Prevention (CDC) provided the strongest evidence to date of an association between ZIKV infection and microcephaly (see, e.g., U.S. Centers for Disease Control and Prevention website, Oliveira et al, *Ultrasound Obstet Gynecol*, 18:167-168 (2016) and Schuler-Faccini et al., *MMWR Morb Mortal Wkly Rep*, 65:59-62 (2016)). Zika infection has also been proposed to cause Guillain-Barré syndrome (GBS), in which an autoimmune response is triggered that damages the nervous system (van den Berg et al., *Ned Tijdschr Geneeskdi*, 160: D155 (2016), Cao-Lormeau et al., *Lancet*, 387:1531-1539 (2016)).

No vaccine exists against ZIKV, and no therapeutics are available. In March of 2015, the World Health Organization (WHO) officially declared ZIKV infection a Public Health Emergency of International Concern (PHEIC) among mounting evidence linking ZIKV infection during pregnancy to microcephaly in newborns. Rapid technological advancements are required to accurately diagnose and combat the spread of this virus.

There exists an urgent need for compositions and methods to identify not only individuals infected with ZIKV, but also to screen blood supplies that may unknowingly contain the virus. The invention provides such compositions and methods.

BRIEF SUMMARY OF THE INVENTION

The invention provides a composition for amplifying and detecting a Zika virus (ZIKV) nucleic acid sequence, which comprises a forward oligonucleotide primer, a reverse oligonucleotide primer, and an oligonucleotide probe, wherein the forward oligonucleotide primer comprises the nucleic acid sequence of SEQ ID NO: 1, the reverse oligonucleotide primer comprises the nucleic acid sequence of SEQ ID NO: 3, and the oligonucleotide probe comprises the nucleic acid sequence of SEQ ID NO: 5.

In one aspect of the above composition, the Zika virus nucleic acid sequence comprises a portion of a nucleic acid sequence that encodes a Zika virus prM protein.

In another aspect of the above composition, the Zika virus nucleic acid sequence comprises the nucleic acid sequence of SEQ ID NO: 21.

The invention also provides a composition for amplifying and detecting a Zika virus nucleic acid sequence, which comprises a forward oligonucleotide primer, a reverse oligonucleotide primer, and an oligonucleotide probe, wherein the forward oligonucleotide primer comprises the nucleic acid sequence of SEQ ID NO: 8, the reverse oligonucleotide primer comprises the nucleic acid sequence of SEQ ID NO: 10, and the oligonucleotide probe comprises the nucleic acid sequence of SEQ ID NO: 11.

In one aspect of the above composition, the Zika virus nucleic acid sequence comprises a portion of a nucleic acid sequence that encodes Zika virus NS3 protein.

In another aspect of the above composition, the Zika virus nucleic acid sequence comprises the nucleic acid sequence of SEQ ID NO: 22.

The invention further provides a composition for amplifying and detecting a Zika virus nucleic acid sequence, which comprises a forward oligonucleotide primer, a reverse oligonucleotide primer, and an oligonucleotide probe, wherein: (a) the forward oligonucleotide primer comprises the nucleic acid sequence of SEQ ID NO: 1 or SEQ ID NO: 2, the reverse oligonucleotide primer comprises the nucleic acid sequence of SEQ ID NO: 3, and the oligonucleotide probe comprises the nucleic acid sequence of SEQ ID NO: 4, (b) the forward oligonucleotide primer comprises the nucleic acid sequence of SEQ ID NO: 6 or SEQ ID NO: 7, the reverse oligonucleotide primer comprises the nucleic acid sequence of SEQ ID NO: 9, and the oligonucleotide probe comprises the nucleic acid sequence of SEQ ID NO: 11, (c) the forward oligonucleotide primer comprises the nucleic acid sequence of SEQ ID NO: 12 or SEQ ID NO: 13, the reverse oligonucleotide primer comprises the nucleic acid sequence of SEQ ID NO: 14, and the oligonucleotide probe comprises the nucleic acid sequence of SEQ ID NO: 15 or SEQ ID NO: 16, or (d) the forward oligonucleotide primer comprises the nucleic acid sequence of SEQ ID NO: 17 or SEQ ID NO: 18, the reverse oligonucleotide primer comprises the nucleic acid sequence of SEQ ID NO: 19, and the oligonucleotide probe comprises the nucleic acid sequence of SEQ ID NO: 20.

In one aspect of the above composition, the forward oligonucleotide primer comprises the nucleic acid sequence of SEQ ID NO: 12 or SEQ ID NO: 13, the reverse oligonucleotide primer comprises the nucleic acid sequence of SEQ ID NO: 14, and the oligonucleotide probe comprises the nucleic acid sequence of SEQ ID NO: 15 or SEQ ID NO: 16.

In another aspect of the above composition, the Zika virus nucleic acid sequence comprises the nucleic acid sequence of SEQ ID NO: 23.

In yet another aspect of the above composition, the forward oligonucleotide primer comprises the nucleic acid sequence of SEQ ID NO: 17 or SEQ ID NO: 18, the reverse oligonucleotide primer comprises the nucleic acid sequence of SEQ ID NO: 19, and the oligonucleotide probe comprises the nucleic acid sequence of SEQ ID NO: 20.

In yet a further aspect of the above composition, the Zika virus nucleic acid sequence comprises the nucleic acid sequence of SEQ ID NO: 24.

In one aspect of the above compositions, the Zika virus is of the African lineage. In another aspect of the above methods, the Zika virus is of the Asian lineage.

In another aspect of the above compositions, the oligonucleotide probe comprises a detectable label.

In another aspect, the invention provides a kit for amplifying and detecting a Zika virus nucleic acid sequence, which comprises: (a) a forward oligonucleotide primer comprising the nucleic acid sequence of SEQ ID NO: 1, (b) a reverse oligonucleotide primer comprising the nucleic acid sequence of SEQ ID NO: 3, (c) an oligonucleotide probe comprising the nucleic acid sequence of SEQ ID NO: 5, and (d) reagents and instructions for amplifying and detecting a Zika virus nucleic acid sequence.

In one aspect of the above kit, the Zika virus nucleic acid sequence comprises a portion of a nucleic acid sequence that encodes a Zika virus prM protein.

In another aspect of the above kit, the Zika virus nucleic acid sequence comprises the nucleic acid sequence of SEQ ID NO: 21.

The invention also provides a kit for amplifying and detecting a Zika virus nucleic acid sequence, which comprises: (a) a forward oligonucleotide primer comprising the nucleic acid sequence of SEQ ID NO: 8, (b) a reverse oligonucleotide primer comprising the nucleic acid sequence of SEQ ID NO: 10, (c) an oligonucleotide probe comprising the nucleic acid sequence of SEQ ID NO: 11, and (d) reagents and instructions for amplifying and detecting a Zika virus nucleic acid sequence.

In one aspect of the above kit, the Zika virus nucleic acid sequence comprises a portion of a nucleic acid sequence that encodes a Zika virus NS3 protein.

In another aspect of the above kit, the Zika virus nucleic acid sequence comprises the nucleic acid sequence of SEQ ID NO: 22.

In another aspect of the above kits, the Zika virus is of the African lineage. In a further aspect of the above kits, the Zika virus is of the Asian lineage.

In another aspect of the above kits, the oligonucleotide probe comprises a detectable label.

The invention also provides a method of detecting a Zika virus nucleic acid sequence in a sample suspected of containing one or more Zika virus nucleic acid sequences, which method comprises: (a) contacting a sample with any of the above-described compositions (b) amplifying any Zika virus nucleic acid sequence that is present in the sample to produce a Zika virus amplicon, (c) hybridizing the oligonucleotide probe to the Zika virus amplicon to produce a probe-amplicon hybrid, wherein the oligonucleotide probe comprises a detectable label, and (d) detecting a signal from the detectable label, wherein the presence of a signal from the detectable label indicates that the sample comprises the probe-amplicon hybrid and the absence of a signal from the detectable label indicates that the sample does not comprise the probe-amplicon hybrid.

The invention also provides a method of detecting a Zika virus nucleic acid sequence in a sample suspected of containing one or more Zika virus nucleic acid sequences, which method comprises: (a) contacting a sample with the any of the above-described kits (b) amplifying any Zika virus nucleic acid sequence that is present in the sample to produce a Zika virus amplicon, (c) hybridizing the oligonucleotide probe to the Zika virus amplicon to produce a probe-amplicon hybrid, wherein the oligonucleotide probe comprises a detectable label, and (d) detecting a signal from the detectable label, wherein the presence of a signal from the detectable label indicates that the sample comprises the probe-amplicon hybrid and the absence of a signal from the detectable label indicates the that the sample does not comprises the probe-amplicon hybrid.

In one aspect of the above methods, the Zika virus amplicon comprises the nucleic acid sequence of SEQ ID NO: 21, SEQ ID NO: 22, SEQ ID NO: 23, or SEQ ID NO: 24.

In yet another aspect of the above methods, the sample is isolated from a human suspected of being infected with a Zika virus.

In another aspect of the above methods, the human is a pregnant female.

In a further aspect of the above methods, the sample is blood.

In yet another aspect of the above methods, the Zika virus is of the African lineage. In an alternative aspect of the above methods, the Zika virus is of the Asian lineage.

DETAILED DESCRIPTION OF THE INVENTION

Figure 1:
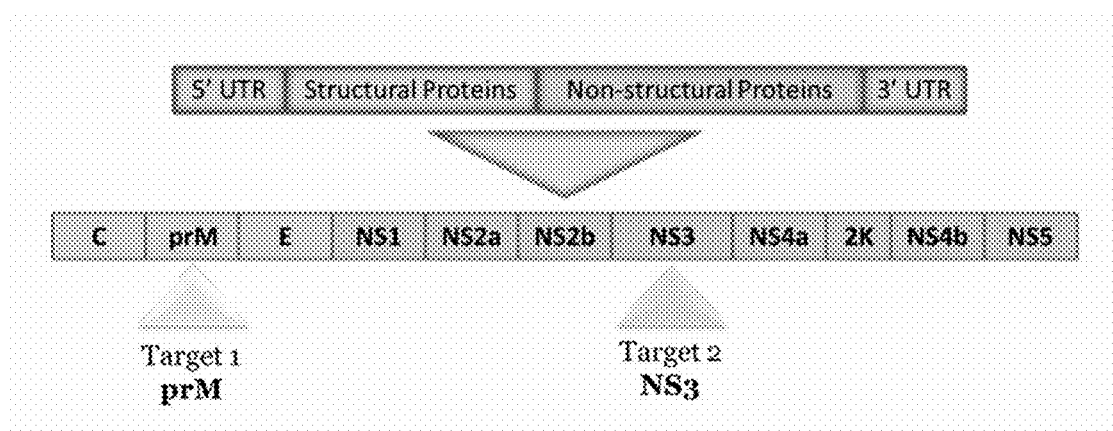
FIG. 1 is a map of the Zika virus genome, identifying the oligonucleotide target regions in the Zika virus assay.
Figure 2:
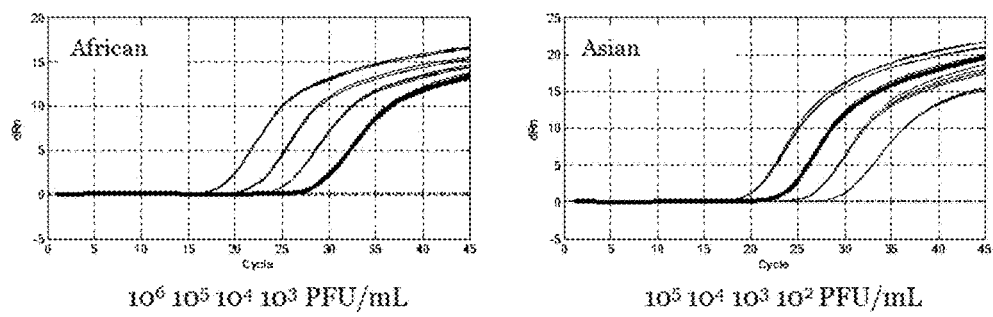
FIG. 2 is a plot from a m2000rt Real Time PCR system (Abbott Laboratories, Abbott Park, Ill.) showing the amplification of the Zika virus prM and NS3 amplicons from plasma samples. The virus was spiked into healthy plasma at a concentration of $10^6$, $10^5$, $10^4$, $10^3$, or $10^2$ plaque forming units (PFU)/ml plasma. Amplification occurred from viruses of the African and the Asian lineages.
Figure 3:
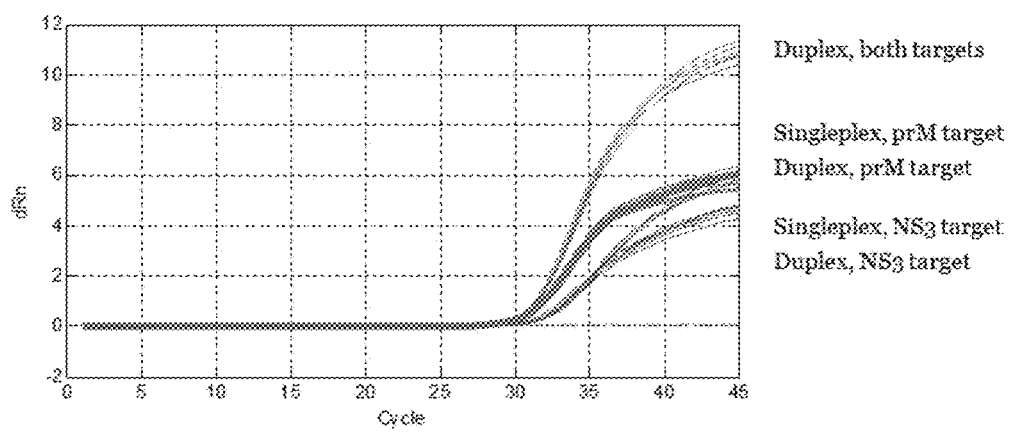
FIG. 3 is a plot from a m2000rt REALTIME™ PCR system (Abbott Molecular, Des Plaines, Ill.) showing the amplification of the Zika virus prM and NS3 amplicons from plasma samples. Amplification and detection were performed on samples containing either a single RNA target and the corresponding primer and probe oligo set (singleplex), a single RNA target and two sets of primer and probe oligos (duplex), or two RNA targets and the corresponding primer and probe oligo sets (duplex).

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The present invention provides compositions, kits, and methods for the amplification and detection of Zika virus nucleic acid sequences in a sample.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention.

As used herein, the term "amplicon" refers to a nucleic acid generated via an amplification reaction. The amplicon is typically double stranded DNA; however, it may be RNA and/or a DNA:RNA hybrid. The amplicon comprises DNA complementary to a sample nucleic acid. In some embodiments, primer pairs are configured to generate amplicons from a sample nucleic acid. As such, the base composition of any given amplicon may include the primer pair, the complement of the primer pair, and the region of a sample nucleic acid that was amplified to generate the amplicon. In one embodiment, the incorporation of the designed primer pair sequences into an amplicon may replace the native sequences at the primer binding site, and complement thereof. In certain embodiments, after amplification of the target region using the primers, the resultant amplicons having the primer sequences are used for subsequent analysis (e.g. base composition determination, for example, via direct sequencing). In some embodiments, the amplicon further comprises a length that is compatible with subsequent analysis.

As used herein, the terms "nucleic acid," "nucleic acid sequence," "oligonucleotide," and "polynucleotide" refer to at least two nucleotides covalently linked together. The depiction of a single strand also defines the sequence of the complementary strand. Thus, an oligonucleotide also encompasses the complementary strand of a depicted single strand. An oligonucleotide also encompasses substantially identical nucleic acids and complements thereof. Oligonucleotides can be single-stranded or double-stranded, or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

The terms "target nucleic acid sequence," "target nucleotide sequence," "target sequence," or "target region" are synonymous and refer to a nucleic acid sequence that is amplified by forward and reverse oligonucleotide primers and/or a nucleic acid sequence contained within an amplified nucleic acid sequence which hybridizes specifically to at least a portion of a probe oligonucleotide using standard hydrogen bonding (i.e., base pairing).

A "Zika virus nucleic acid sequence" is a nucleic acid sequence that is naturally found in a Zika virus genome, or a nucleic acid sequence that is derived from or based on a Zika virus genome and shares at least 90% sequence identity (e.g., 90%, 91%, 92%, 93%, 94%, 95%, 96%, 97%, 98%, 99%, 100% sequence identity) to a naturally occurring Zika virus nucleic acid sequence.

"Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of an oligonucleotide complementary to a target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Label" and "detectable label" mean a moiety attached, directly or indirectly, to an oligonucleotide probe to render the formation of a hybrid between the probe and a target nucleic acid sequence (e.g., a probe-amplicon hybrid), and the oligonucleotide probe so labeled is referred to as "detectably-labeled." A label can produce a signal that is detectable, e.g., by visual or instrumental means. In this aspect, a label can be any signal-generating moiety, and sometimes is referred to herein as a reporter group. As used herein, the label (or signal-generating moiety) produces a measurable signal which is detectable by external means, e.g., by the measurement of fluorescence.

"Oligonucleotide primer," as used herein, refers to an oligonucleotide capable of acting as a point of initiation for DNA synthesis under suitable conditions. Suitable conditions include those in which hybridization of the oligonucleotide to a template nucleic acid occurs, and synthesis or amplification of the target sequence occurs, in the presence of four different nucleoside triphosphates and an agent for extension (e.g., a DNA polymerase) in an appropriate buffer and at a suitable temperature. A "forward oligonucleotide primer" or "sense primer," as used herein, refers to an oligonucleotide capable of acting as a point of initiation for DNA synthesis at the 5' end of a target nucleic acid sequence. A "reverse oligonucleotide primer" or "anti-sense primer," as used herein, refers to an oligonucleotide capable of acting as a point of initiation for DNA synthesis at the 3' end of a target nucleic acid sequence.

"Oligonucleotide probe," as used herein, refers to an oligonucleotide that hybridizes specifically to a target sequence in a nucleic acid, preferably in an amplified nucleic acid, under conditions that promote hybridization, to form a detectable hybrid. A probe may contain a detectable moiety (e.g., a label) which either may be attached to the end(s) of the probe or may be internal. The nucleotides of the probe which hybridize to the target nucleic acid sequence need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). An oligonucleotide probe may comprise target-specific sequences and other sequences that contribute to three-dimensional conformation of the probe (e.g., as described in, e.g., U.S. Pat. Nos. 5,118,801 and 5,312,728).

"Polymerase Chain Reaction (PCR)" refers to the enzymatic reaction in which DNA fragments are synthesized and amplified from a substrate DNA in vitro. The reaction typically involves the use of two synthetic oligonucleotide primers, and may optionally include a synthetic oligonucleotide probe, which are complementary to nucleotide sequences in the substrate DNA which are separated by a short distance of a few hundred to a few thousand base pairs, and the use of a thermostable DNA polymerase. The chain reaction consists of a series of 10 to 40 cycles. In each cycle, the substrate DNA is first denatured at high temperature. After cooling down, synthetic primers which are present in vast excess, hybridize to the substrate DNA to form double-stranded structures along complementary nucleotide sequences. The primer-substrate DNA complexes will then serve as initiation sites for a DNA synthesis reaction catalyzed by a DNA polymerase, resulting in the synthesis of a new DNA strand complementary to the substrate DNA strand. The synthesis process is repeated with each additional cycle, creating an amplified product of the substrate DNA.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

"Sample," "biological sample," "test sample," "specimen," "sample from a subject," and "patient sample" as used herein may be used interchangeable and may be a sample of blood, tissue, saliva, urine, semen, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluids may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose).

Archival tissues, such as those having treatment or outcome history, may also be used. Protein or nucleotide isolation and/or purification may not be necessary. Methods well-known in the art for collecting, handling and processing urine, blood, serum and plasma, and other body fluids, are used in the practice of the present disclosure.

As used herein, the terms "subject" and "patient" are used interchangeably irrespective of whether the subject has been diagnosed with Zika virus infection. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). The subject may also be a mosquito, such as a mosquito of the *Aedes* genus (e.g., *A. aegypti* and *A. albopictus* mosquito species). Preferably, the subject is a human.

2. Zika Virus (ZIKV)

Zika virus (ZIKV) is a member of the Flavivirus genus of viruses, which also includes West Nile virus, dengue virus, yellow fever virus, and tick-borne encephalitis virus. Like other Flaviviruses, ZIKV is transmitted through a bite from an infected mosquito of the *Aedes* genus, most often by the *A. aegypti* and *A. albopictus* mosquito species; other mosquito species may also be involved in transmitting the virus. ZIKV is an enveloped icosahedral virus containing a single-stranded, positive-sense RNA genome, which is released into the cytoplasm of an infected host cell. The genome is translated into a single polyprotein, which is cleaved to generate structural and non-structural proteins. The Zika virus structural proteins include the anchored capsid protein C (ancC), core (C) protein, membrane glycoprotein precursor M (prM), protein pr (pr), membrane protein (M), and envelope (E) protein; the non-structural (NS) proteins include NS1, NS2A, NS2B, NS3 (helicase/viral protease), NS4A, NS4B, NS5 (RNA-dependent RNA polymerase), and protein 2K (2K).

The first identified isolate of Zika virus was the MR 766 strain (Uganda 1947), the genome of which has been sequenced and is publicly available (NCBI Accession No. AY632535). Phylogenetic studies have identified two lineages that extend from the MR 766 strain: the African (East African and West African) and the Asian lineages. The African lineage includes the strains IbH 30656 (Nigeria 1968; NCBI Accession No. HQ234500.1) and ArD 41519 (Senegal 1984; NCBI Accession No. HQ234501), and the Asian lineage includes the strains P6-740 (Malaysia 1966; NCBI Accession No. HQ234499), EC Yap (Micronesia 2007; NCBI Accession No. EU545988), and FSS13025 (Cambodia 2010; NCBI Accession No. KU955593). Additional known strains of ZIKV and corresponding phylogenetic analysis are described in detail in, e.g., Haddow et al., *PLoS Negl Trop Dis*, 6:e1477 (2012).

Additional phylogenetic studies have indicated that the Zika viruses currently circulating in the Western Hemisphere are 89% identical (as a group) to viruses of the African lineage, and that the percent nucleotide identity among all of the Western Hemisphere viruses is >99% (see, e.g., Lanciotti et al., *Emerg Infect Dis*, 22:933-935 (2016)). The compositions and methods described herein can be used to detect one or more nucleic acid sequences of any Zika virus strain or lineage known in the art. One skilled in the art will appreciate that new strains and genotypes of ZIKV may be discovered or emerge in the future. The use of the compositions and methods described herein to amplify and/or detect nucleic acids from new ZIKV genotypes is also considered to be within the scope of the present invention. In one embodiment, the compositions and methods described herein can be used to amplify and detect one or more nucleic acids of Zika virus of the African lineage. In another embodiment, the compositions and methods described herein can be used to amplify and detect one or more nucleic acids of a Zika virus of the Asian lineage.

3. Oligonucleotide Primers and Probes

The compositions described herein comprise a forward oligonucleotide primer, a reverse oligonucleotide primer, and an oligonucleotide probe. As discussed above, the oligonucleotide primers and probes can be designed to amplify and detect any suitable nucleic acid sequence of any suitable Zika virus, such as, for example, strains in the African lineage (e.g. MR 766 and IbH 30656), and strains in the Asian lineage (e.g., ArD 41519, P6-740, FS13025, and EC Yap). Oligonucleotide primers and probes can be designed and synthesized using routine molecular biology techniques known in the art, such as those described in, e.g., Tang et al., *Biotechniques*, 40(6): 759-763 (2006); Espelund et al., *Nuc. Acids. Res.*, 18(20): 6157-6158 (1990); Sambrook et al., *Molecular Cloning: A Laboratory Manual*, 4th ed., Cold Spring Harbor Press, Cold Spring Harbor, N.Y. (2012); and Ausubel et al., *Current Protocols in Molecular Biology*, John Wiley & Sons, New York (2016). Primer pairs also can be designed using a variety of tools, such as the Primer-BLAST tool provided by the National Center of Biotechnology Information (NCBI).

It will be appreciated that the oligonucleotide primers and oligonucleotide probes described herein have a melting temperature ($T_M$) in the range 45° C. to 80° C. In accordance with the present invention, the oligonucleotides specifically hybridize to a target ZIKV nucleic acid sequence without exhibiting significant hybridization to non-ZIKV nucleic acids. In addition, the oligonucleotides are selected such that they hybridize to conserved regions in the ZIKV genome, thus minimizing mismatches with the target sequence, especially at the 3' end. This selection ensures that the oligonucleotides are capable of hybridizing to ZIKV nucleic acids from all genotypes and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

The oligonucleotide primers and probes described herein can amplify and detect any suitable Zika virus nucleic acid sequence, or any suitable combination of Zika virus nucleic acid sequences. For example, the oligonucleotide primers and probes described herein can amplify and detect one or more Zika virus nucleic acid sequences encoding any one (or combination of) the Zika virus proteins listed above. Alternatively, the oligonucleotide primers and probes described herein can amplify and detect any portion, as defined herein, of a protein-encoding Zika virus nucleic acid sequence. For example, the oligonucleotide primers and probes described herein can amplify and detect a Zika virus nucleic acid sequence that comprises about 40 or more (e.g., 40 or more, 50 or more, 60 or more, 70 or more, or 80 or more) nucleotides, but less than about 200 (e.g., 200 or less, 190 or less, 180 or less, 170 or less, 160 or less, 150 or less, 140 or less, 130 or less, 120 or less, 110 or less, 100 or less, or 90 or less) nucleotides. Preferably, the oligonucleotide primers and probes described herein amplifies and detects a Zika virus nucleic acid sequence that comprises about 50 to about 150 nucleotides (e.g., 55, 65, 75, 85, 95, 105, 115, 125, 135, or 145 nucleotides), about 60 to about 140 nucleotides (e.g., about 60, 70, 80, 90, 100, 110, 120, 130, or 140 nucleotides), or a range defined by any two of the foregoing values.

In one embodiment, the oligonucleotide primers and probes described herein amplify and detect a portion of a Zika virus nucleic acid sequence that encodes the prM protein, a portion of a Zika virus nucleic acid sequence that encodes the NS3 protein, a portion of a Zika virus nucleic acid sequence that encodes the NS5 protein, and/or a portion of a Zika virus nucleic acid sequence that encodes the core protein. More preferably, the oligonucleotide primers and probes described herein amplify and detect a portion of a Zika virus nucleic acid sequence that encodes the prM protein and/or a portion of a Zika virus nucleic acid sequence that encodes the NS3 protein. For example, the composition can comprise a forward oligonucleotide primer comprising the nucleic acid sequence of SEQ ID NO: 1 or SEQ ID NO: 2, a reverse oligonucleotide primer comprising the nucleic acid sequence of SEQ ID NO: 3, and an oligonucleotide probe comprising the nucleic acid sequence of SEQ ID NO: 4 or SEQ ID NO: 5, which amplifies and detects a portion of a Zika virus nucleic acid sequence that encodes the prM protein comprising SEQ ID NO 21. Preferably, the composition comprises a forward oligonucleotide primer comprising the nucleic acid sequence of SEQ ID NO: 1, a reverse oligonucleotide primer comprising the nucleic acid sequence of SEQ ID NO: 3, and an oligonucleotide probe comprising the nucleic acid sequence of SEQ ID NO: 5.

In addition or alternatively, the composition can comprise a forward oligonucleotide primer comprising the nucleic acid sequence of SEQ ID NO: 6, SEQ ID NO: 7, or SEQ ID NO: 8, a reverse oligonucleotide primer comprising the nucleic acid sequence of SEQ ID NO: 9 or SEQ ID NO: 10, and an oligonucleotide probe comprising the nucleic acid sequence of SEQ ID NO: 11, which amplifies and detects a portion of a Zika virus nucleic acid sequence that encodes the NS3 protein comprising SEQ ID NO: 22. Preferably, the composition can comprise a forward oligonucleotide primer comprising the nucleic acid sequence of SEQ ID NO: 8, a reverse oligonucleotide primer comprising the nucleic acid sequence of SEQ ID NO: 10, and an oligonucleotide probe comprising the nucleic acid sequence of SEQ ID NO: 11.

In another embodiment, the composition can comprise a forward oligonucleotide primer comprising the nucleic acid sequence of SEQ ID NO: 12 or SEQ ID NO: 13, a reverse oligonucleotide primer comprising the nucleic acid sequence of SEQ ID NO: 14, and an oligonucleotide probe comprising the nucleic acid sequence of SEQ ID NO: 15 or SEQ ID NO: 16, which amplifies and detects a portion of a Zika virus nucleic acid sequence that encodes the NS5 protein comprising SEQ ID NO: 23.

In another embodiment, the composition can comprise a forward oligonucleotide primer comprising the nucleic acid sequence of SEQ ID NO: 17 or SEQ ID NO: 18, a reverse oligonucleotide primer comprising the nucleic acid sequence of SEQ ID NO: 19, and an oligonucleotide probe comprising the nucleic acid sequence of SEQ ID NO: 20, which amplifies and detects a portion of a Zika virus nucleic acid sequence that encodes the core protein comprising SEQ ID NO: 24.

The specific combinations of oligonucleotide primers and probes described above also are set forth in Tables 1-4 below.

TABLE 1 prM Primer and Probe Sequences

| prM Oligonucleotide | Nucleic Acid Sequence | SEQ ID NO. |
|---|---|---|
| Forward primer 658-1 | GAACCAGATGACGTCGATTG | 1 |
| Forward primer 658-2 | GAACCAGATGATGTCGATTG | 2 |
| Reverse primer 658-1 | CAGGTTCCGTACACAACCCAAGT | 3 |
| Zika probe 658-1 | TGGTGCAACACGACATC | 4 |
| Zika probe 658-2b | TGGTGCAACACGACGTC | 5 |

TABLE 2

NS3 Primer and Probe Sequences

| NS3 Oligonucleotide | Nucleic Acid Sequence | SEQ ID NO. |
|---|---|---|
| Forward primer 6007-1 | GGCAGGAACCCTAAGAAACCT | 6 |
| Forward primer 6007-2 | GGCAGGAACCCTAACAAACCT | 7 |
| Forward primer 6007-4 | GGCAGGAATCCCAACAAACCT | 8 |
| Reverse primer 6007-1 | CTATGAGGCCATCCTGGAGGTA | 9 |
| Reverse primer 6007-2 | CTATGAGGCCATCTTGGAGGTA | 10 |
| Zika probe 6007-1 | TGGCTTGAAGCAAGAATGCT | 11 |

TABLE 3

NS5 Primer and Probe Sequences

| NS5 Oligonucleotide | Nucleic Acid Sequence | SEQ ID NO. |
|---|---|---|
| Forward primer 9870-1 | GGATGGGAGATCCATTGTGGT | 12 |
| Forward primer 9870-2 | GGATGGTAGATCCATTGTGGT | 13 |
| Reverse primer 9870-1 | CTCCCGGATGCTCCATCC | 14 |
| Zika probe 9870-1 | CCACCAAGATGAACTGATTG | 15 |
| Zika probe 9870-2 | CCACCAAGATGAATTGATTG | 16 |

TABLE 4

Core Primer and Probe Sequences

| Core Oligonucleotide | Nucleic Acid Sequence | SEQ ID NO. |
|---|---|---|
| Forward primer 307-1 | GCCTCATCAACAGATGGGTTC | 17 |
| Forward primer 307-2 | GTGGGGAAAAAGAGGCTATGGA | 18 |

TABLE 4-continued

Core Primer and Probe Sequences

| Core Oligonucleotide | Nucleic Acid Sequence | SEQ ID NO. |
|---|---|---|
| Reverse primer 307-1 | CTCTTCCTCTCCTTCCTAGCATTGAT | 19 |
| Zika probe 307-1 | GCTGCCATGTTGAGAAT | 20 |

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C\equiv CH$. The one or more propyne-modified bases may include, for example, 5-(1-propynyl)-2'-deoxy-Uridine (pdU) and/or 5-(1-propynyl)-2'-deoxyCytidine (pdC). In one embodiment, for example, the Zika probe 658-2b (SEQ ID NO: 5) sequence set forth in Table 1 may comprise the propyne modified sequence of TGG-pdU-G-pdC-AA-pdC-A-pdC-GACGT-pdC (SEQ ID NO: 25).

The oligonucleotide probe may additionally comprise a detectable label. Any suitable detectable label that can be conjugated or linked to a probe in order to detect a probe binding to its target can be used, many of which are known in the art. In one embodiment, the detectable label may include one that can be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present invention, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may also be one that can be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squaraine-family dye, chelated lanthanide-family dye, azo-family dye, triphenylmethane-family dye, or a BODIPY®-family dye. Examples of fluorophores include, but are not limited to, FAM™, HEX™, JOE™, NED™, PET®, ROX™, TAMRA™, TET™, TEXAS RED®, and VIC®. One skilled in the art will appreciate that directly detectable labels may require additional components, such as substrates, triggering reagents, light, and the like, to enable detection of the label.

In an embodiment, the oligonucleotide probe may also comprise at least one quencher. The quencher may be selected from any suitable quencher known in the art, such as, for example, BLACK HOLE QUENCHER® 1 (BHQ-1®), BLACK HOLE QUENCHER® 2 (BHQ-2®), IOWA BLACK® FQ, and IOWA BLACK® RQ. In an embodiment, the oligonucleotide probe may comprise a detectable label and a quencher. For example, the oligonucleotide probe may comprise a FAM fluorophore and a BHQ-1 quencher.

As discussed above, depending on the combination of oligonucleotide primers and probes selected, the compositions described herein can may be used to amplify and detect a Zika virus nucleic acid amplicon comprising the nucleic acid sequence of SEQ ID NO: 21 (prM), SEQ ID NO: 22 (NS3), SEQ ID NO: 23 (NS5), SEQ ID NO: 24 (core), or any combination thereof.

For example, two or more Zika virus nucleic acid sequences or amplicons can be detected simultaneously in a single reaction using a combination of the oligonucleotide primer and probe sets described above. In an embodiment, a sample may be contacted with primer/probe sets that amplify and detect a portion of a nucleic acid sequence encoding Zika virus prM protein and primer/probe sets that amplify and detect a portion of a nucleic acid sequence encoding Zika virus NS3 protein, along with appropriate reagents.

In another embodiment, the inventive compositions can comprise oligonucleotide primers and probes that comprise a nucleic acid sequence that is at least 80% (e.g., 80%, 81%, 82%, 83%, 84%, 85%, 86%, 87%, 88%, 89%), at least 90% identical (e.g., 90%, 91%, 92%, 93%, 94% identical), and preferably at least 95% identical (e.g., 95%, 96%, 97%, 98%, 99%, or 100% identical) to any of the foregoing nucleic acid sequences. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

4. Kit for Amplifying and Detecting a Zika Virus Nucleic Acid Sequence

The invention also provides a kit for amplifying and detecting a Zika virus nucleic acid sequence. The kit comprises a forward oligonucleotide primer, a reverse oligonucleotide primer, an oligonucleotide probe, and reagents and instructions for amplifying and detecting a Zika virus nucleic acid sequence. Descriptions of the oligonucleotide primers and oligonucleotide probes set forth herein with respect to the aforementioned compositions also are applicable to those same aspects of the kits described herein. Examples of suitable reagents for inclusion in the kit (in addition to the oligonucleotide primers and probes described herein) include conventional reagents employed in nucleic acid amplification reactions, such as, for example, one or more enzymes having polymerase activity, enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate and deoxythymidine triphosphate) a blocking agent, a labeling agent, and the like. Many such reagents are described herein or otherwise known in the art and commercially available.

In one embodiment, the kit may comprise (a) a forward oligonucleotide primer comprising the nucleic acid sequence of SEQ ID NO: 1, (b) a reverse oligonucleotide primer comprising the nucleic acid sequence of SEQ ID NO: 3, (c) an oligonucleotide probe comprising the nucleic acid sequence of SEQ ID NO: 5, and (d) reagents and instructions for amplifying and detecting a Zika virus nucleic acid sequence. In this embodiment, the kit amplifies and detects a portion of a nucleic acid sequence that encodes Zika virus prM protein, such as the nucleic acid sequence of SEQ ID NO: 21. In another embodiment, the kit may comprise (a) a forward oligonucleotide primer comprising the nucleic acid sequence of SEQ ID NO: 8, (b) a reverse oligonucleotide primer comprising the nucleic acid sequence of SEQ ID NO: 10, (c) an oligonucleotide probe comprising the nucleic acid sequence of SEQ ID NO: 11, and (d) reagents and instructions for amplifying and detecting a Zika virus nucleic acid sequence. In this embodiment, the kit amplifies and detects a portion of a nucleic acid sequence that encodes Zika virus NS3 protein, such as the nucleic acid sequence of SEQ ID NO: 22.

5. Method for Amplifying and Detecting Zika Virus Nucleic Acid Sequence

The disclosure provides a method of detecting a Zika virus nucleic acid sequence in a sample suspected of containing one or more Zika virus nucleic acid sequences, which method comprises (a) contacting a sample with a composition comprising oligonucleotide primers and oligonucleotide probes as described herein, (b) amplifying any Zika virus nucleic acid sequence that is present in the sample to produce a Zika virus amplicon, and (c) hybridizing the oligonucleotide probe to the Zika virus amplicon to produce a probe-amplicon hybrid, and (d) detecting the probe-amplicon hybrid. Descriptions of the oligonucleotide primers and oligonucleotide probes set forth herein with respect to the aforementioned compositions also are applicable to those same aspects of the inventive method.

A sample (as defined herein) is "suspected" of containing one or more Zika virus nucleic acid sequences if the sample is obtained from a subject, preferably a human, suspected of being infected with a Zika virus. A subject is suspected of being infected with a Zika virus if the subject has spent any amount of time, or has been in contact with another subject who has spent any amount of time, in any country with epidemic or endemic Zika virus and has been bitten by a mosquito (preferably a mosquito in the Aedes genus). Such countries include, but are not limited to, Argentina, Aruba, Barbados, Belize, Bolivia, Bonaire, Brazil, Colombia, Puerto Rico, Costa Rica, Cuba, Curacao, Dominica, Dominican Republic, Ecuador, El Salvador, French Guiana, Grenada, Guadeloupe, Guatemala, Guyana, Haiti, Honduras, Jamaica, Martinique, Mexico, Nicaragua, Panama, Paraguay, Peru, Saint Barthelemy, Saint Lucia, Saint Martin, Saint Vincent and the Grenadines, Saint Maarten, Suriname, Trinidad and Tobago, U.S. Virgin Islands, Venezuela, American Samoa, Fiji, Kosrae, Federated States of Micronesia, Marshall Islands, New Caledonia, Papua New Guinea, Samoa, Tonga, and Cape Verde.

The sample can be any suitable sample obtained from any suitable subject, typically and preferably a human. In one embodiment, the sample is isolated from a pregnant female. Preferably, the sample is a blood sample isolated from a pregnant female. In this manner, the sample may be contacted with the compositions or kits described herein using methods routinely employed in clinical diagnostic settings.

The inventive method further comprises amplifying any Zika virus nucleic acids present in the sample to produce a Zika virus amplicon, which amplification is mediated by the oligonucleotide primers present in the composition. Amplifying any Zika virus nucleic acids in the sample can be performed using any suitable nucleic acid sequence amplification method known in the art, including, but not limited to, polymerase chain reaction (PCR), reverse-transcriptase PCR (RT-PCR), transcription-mediated amplification (TMA), rolling circle amplification, nucleic acid sequence based amplification (NASBA), strand displacement amplification (SDA), and ligase chain reaction (LCR).

Because Zika virus comprises an RNA genome, amplification of the Zika virus nucleic acid sequence desirably is performed using RT-PCR. "RT-PCR," as used herein, refers to the enzymatic reaction in which complimentary DNA (cDNA) fragments are synthesized from a substrate RNA template. The reaction typically involves the use of a synthetic oligonucleotide primer, which is complementary to nucleotide sequences in the substrate RNA, and the use of a reverse transcriptase enzyme. The reaction consists of one cycle, in which the oligonucleotide primers which are present in vast excess, hybridize to the substrate RNA to form double-stranded structures along complementary nucleotide sequences. The primer-substrate DNA:RNA complexes will then serve as initiation sites for a cDNA synthesis reaction catalyzed by reverse transcriptase, resulting in the synthesis of a cDNA strand complementary to the RNA strand. The RNA may be a messenger RNA (mRNA), transfer RNA (tRNA), genomic RNA (gRNA), ribosomal RNA (rRNA), or a small nuclear RNA (snRNA). Methods and reagents for RT-PCR well known in the art and commercially available from a variety of sources (see, e.g., Freeman, W. M. et al., *Biotechniques*, 26(1): 112-122, 142-125 (1999); Joyce, C., *Methods Mol. Biol.*, 193: 83-92 (2002); and O'Connell, J. (ed.), *RT-PCR Protocols*, 1$^{st}$ Ed., Springer-Verlag, New York, N.Y. (2010)). Reverse transcription can be performed using one-step or two-step techniques known in the art, such as, for example, by using reverse transcription kits available from APPLIED BIOSYSTEMS™, LIFE TECHNOLOGIES™, QIAGEN™, PROMEGA™, and INVITROGEN™.

In embodiments where a sample contains one or more Zika virus nucleic acid sequences that are amplified by the oligonucleotide primers described herein, the amplification reaction will produce one or more Zika virus amplicons (as defined herein). In one embodiment, the Zika virus amplicon can comprise any one or combination of the following nucleic acid sequences: SEQ ID NO: 21, SEQ ID NO: 22, SEQ ID NO: 23, and/or SEQ ID NO: 24.

Following amplification of any Zika virus nucleic acid sequence that is present in the sample, the inventive method further comprises hybridizing the oligonucleotide probe to the Zika virus amplicon to produce a probe-amplicon hybrid, wherein the oligonucleotide probe comprises a detectable label. As discussed above, a reaction mixture comprising a Zika virus amplicon may be contacted with an oligonucleotide probe, as described herein, that preferentially hybridizes to a target nucleic acid sequence of the amplicon, or the complement thereof, under stringent hybridization and wash conditions, thereby forming a probe-amplicon hybrid duplex that is stable for detection. Stringent hybridization conditions are described herein, and desirably minimize appreciable amounts of detectable binding of the oligonucleotide probe to non-specific or non-target nucleic acid sequences. It will be appreciated, however, that some amount of mismatch or sequence overhang can be tolerated without affecting stringency or specificity of probe hybridization. In one embodiment, hybridization of an oligonucleotide probe to a Zika virus amplicon can occur at a temperature of about 60° C. and a salt concentration between about 0.6-0.9 M. Salts that can be used in the hybridization reaction include, for example, lithium chloride, sodium chloride, and sodium citrate. Alternatively, high stringency hybridization conditions can include 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. Any suitable method and conditions for hybridizing an oligonucleotide probe to a Zika virus amplicon to produce a probe-amplicon hybrid known in the art can be used in the inventive method, however.

Following hybridization of the oligonucleotide probe to a Zika virus amplicon, the method comprises detecting a signal from the detectable label present on the oligonucleotide probe, wherein the presence of a signal from the detectable label indicates that the sample comprises the probe-amplicon hybrid (and therefore, a Zika virus nucleic acid sequence) and the absence of a signal from the detectable label indicates that the sample does not comprise the probe-amplicon hybrid.

7. Examples

The following example further illustrates the invention but, of course, should not be construed as in any way limiting its scope.

Example 1

This example demonstrates the development and validation of oligonucleotide primers and probes to amplify and detect Zika virus nucleic acid sequences in a sample.

Primer and probe oligonucleotides were designed to target the Zika virus prM gene (Table 1), the NS3 gene (Table 2), the NS5 gene (Table 3), and the C gene (Table 4). The prM and NS3 targets were specifically designed to target highly conserved regions of each gene (see FIG. 1) in order to ensure that the assay will be effective as ZIKV evolves.

A standard curve was generated for the prM and NS3 target sequences to allow for the quantification of these genes in samples. Synthetic double stranded DNA corresponding to the prM and NS3 target sequences were synthesized as gene fragments and used as templates for in vitro transcription. The resulting RNA transcripts were treated with DNase to remove any residual template DNA, and then the RNA copy number of each transcript preparation was calculated based on the A260 value and the predicted size of the transcripts. An equal copy number/mL of the prM and NS3 transcripts were combined together to create standard curve stocks. The stocks were then serially diluted to create standard curves.

The standard curves for the prM and NS3 regions of interest were then used to calculate the concentration of Zika virus cultures for PRVABC59 (Puerto Rico, Asian lineage), SPH2015 (Brazil, Asian lineage), and MR766 (Uganda, African lineage). The tested oligonucleotide primer and probe combinations exhibited robust amplification of prM and NS3 in the Zika viruses of both the African and Asian lineages, as shown in FIG. 2. Both prM and NS3 were detected with the fluorophore FAM, resulting in overlapping amplification curves at each concentration of template virus.

Additional studies were performed testing the amplification of each of the prM and NS3 genes separately and in combination. For these tests, a master mix was used containing: (1) the RNA target of only one gene and the corresponding primer and probe oligos (e.g., prM RNA target with prM oligos, or NS3 RNA target with NS3 oligos); (2) the RNA target for only one gene and the primer and probe oligos for both genes (e.g., prM RNA target and the primer and probe oligos for both prM and NS3, or NS3 RNA target and the primer and probe oligos for both prM and NS3); or (3) the RNA targets for both genes and primer and probe oligos for both genes (e.g., prM and NS3 RNA targets and the oliogs for prM and NS3). Efficient amplification occurred in all conditions tested (FIG. 3), although amplification of both target genes with both sets of primer and probe oligos yielded the most robust amplification. An RNA sequence unrelated to the Zika virus target sequences was introduced into each specimen at the beginning of sample preparation, which is simultaneously processed and amplified by RT-PCR, and serves as an internal control (IC) to demonstrate that the process has completed correctly for each specimen and control.

Next, the limit of detection for the assay was defined for each sample matrix (serum, plasma, urine, or whole blood). The limit of detection was defined as the concentration (copy number/mL) at which ? 95% of the replicates tested positive for Zika virus. This calculation was determined by testing panels of the Zika virus PRVABC59 strain diluted in each respective sample matrix. The limit of detection was determined to be 30 copies/mL in serum, 40 copies/mL in plasma and urine, and 120 copies/mL in whole blood.

The results of this example demonstrate the generation of standard curves for Zika virus prM and NS3 genes and the amplification of both genes simultaneously in a sample.

Example 2

This example demonstrates the specificity of the method described herein for detecting Zika viruses of the Asian and African lineages.

The ability of the Zika virus detection method described herein to detect both the African and Asian lineages was assessed by quantifying three samples that each contained a different strain of Zika virus diluted to 80 copies/mL (i.e., twice the limit of detection for plasma). The assay was able to detect the Zika virus strains PRVABC59 (Asian) at 37.26 cycles, SPH2015 (Asian) at 37.23 cycles, and MR766 (African) at 37.00 cycles, as shown in Table 5. The similar cycle number (CN) values demonstrate equivalent detection of both the African and Asian lineages.

TABLE 5

| Zika Strain/Isolate | Source/Sample Type | Lineage | Mean CN |
|---|---|---|---|
| Zika virus PRVABC59 | Puerto Rico/Virus culture supernatant | Asian | 37.26 |
| Zika virus SPH 2015 | Brazil/Virus culture supernatant | Asian | 37.23 |
| Zika virus MR766 | Uganda/Virus culture supernatant | African | 37.00 |

The potential of the detection assay to exhibit cross-reactivity with closely related viruses or other blood-borne pathogens was evaluated by testing viruses or purified nucleic acids at high concentrations. Briefly, virus stocks of 4 strains of dengue virus (CDC, New Guinea C, H87, and H241), yellow fever virus (17D), West Nile virus (NY2001-6263), chikungunya virus (R80422), and human parvovirus B19 were purchased from Zeptometrix (Buffalo, N.Y.). Plasmodium falciparum (strain 3D7) DNA and lyophilized Mayaro virus (strain TRVL 15537) were purchased from the American Type Culture Collection (ATCC) (Manassas, Va.). Samples of each virus or pathogen were diluted into purified protein matrix, and a reconstituted Mayaro virus suspension was diluted into negative plasma. Nucleic acid was then extracted from each sample and prepared for RT-PCR. A sample of Plasmodium falciparum DNA was added directly into a well of the PCR plate containing master mix prior to the start of the cycling conditions. The results of the PCR reactions showed that no cross-reactivity with the selected pathogens was observed using the Zika virus detection assay at the concentrations tested.

Next, in silico analysis of the primer and probe sequences was performed to verify sequence homology with the corresponding prM and NS3 target regions identified in 48 known Zika virus genomes. Overall, the prM primer and probe sequences demonstrated 94% to 100% sequence identity for the prM targets, and the NS3 primer and probe sequences demonstrated 86% to 100% sequence identity for the NS3 targets. However, the in silico study revealed that the forward primer for the prM target shared complete homology to dengue virus, serotype 1. Given that dengue is endemic in many of the same regions as Zika virus, and that both Zika and dengue share the same vector for transmission, a study was conducted to assess whether high levels of dengue virus in clinical specimens would interfere with the detection of Zika virus by this assay.

A dengue virus serotype 1 positive specimen was purchased from the American Red Cross (Gaithersburg, Md.), and diluted to a concentration of $1\times10^5$ copies/mL in human plasma. The diluted virus was tested either alone, or in combination with 80 or 1000 copies/mL of Zika virus. Overall, no interference was observed in the efficacy or specificity of the assay in the presence of $1\times10^5$ copies/mL of dengue virus, despite the shared homology of the Zika virus primer and dengue virus.

The primer and probe sequences in the Zika virus detection method described herein were also subject to a BLAST analysis against all available sequences for the organisms listed in Table 6, using the following parameters: blastn, maximum target sequence=10,000, word size=7, expect threshold=1,000, Match/Mismatch score=1, −3, and Gap Costs=Existence: 5 Extension: 2. Based on the results of this analysis, it was concluded that there is limited opportunity for cross-reactivity to result in false-positive reporting.

TABLE 6

| Organism | | Tax ID |
|---|---|---|
| Bacteria | Borrelia burgdorferi | 64895 |
| | E coli NGF1 | 562 |
| | E coli 0157:H7 | 386585 |
| | Leptospira | 171 |
| | Rickettsia | 780 |
| | Salmonella typhi | 527001 |
| | Group A Streptococcus | 36470 |
| Protozoa | Plasmodium falciparum | 5833 |
| | Plasmodium sp | 5820 |
| | Tyrpanosoma cruzi | 5693 |
| Trematode | Schistosoma | 6183 |
| Flavivirus | Dengue virus 1 (DENV-1) | 11053 |
| | Dengue virus 2 (DENV-2) | 11060 |
| | Dengue virus 3 (DENV-3) | 11069 |
| | Dengue virus 4 (DENV-4) | 11070 |
| | Hepatitis C virus | 11102 |
| | Japanese encephalitis virus | 11071 |
| | St Louis encephalitis virus | 11080 |
| | Spondweni virus | 64318 |
| | Yellow fever virus | 40005 |
| | Yellow fever virus vaccine | 11090 |
| | West Nile virus | 11082 |
| Alphavirus | Barmah Forest virus | 11020 |
| | Chikungunya | 37124 |
| | Eastern equine encephalitis virus | 11021 |
| | Mayaro virus | 59301 |
| | O'nyong-nyong virus | 11027 |
| | Ross River virus | 11029 |
| | Western equine encephalitis virus | 11039 |
| Other Virus | Adenovirus B | 108098 |
| | Adenovirus B1 | 565302 |
| | Adenovirus C | 129951 |
| | Adenovirus D | 130310 |
| | Adenovirus 7 | 10519 |
| | Enterovirus | 12059 |
| | Epstein-Barr virus | 10376 |
| | Hepatitis A virus vaccine | 208726 |
| | Hepatitis B virus | 10407 |
| | Human Cytomegalovirus | 10358 |
| | Human immunodeficiency virus 1 | 11676 |
| | Human parvovirus | 10798 |
| | Measles virus | 11234 |
| | Rubella virus | 11041 |
| | Varicella-zoster virus | 10335 |

Example 3

This example demonstrates the efficacy of the Zika virus detection method described herein (also referred to as the "ZIKV assay") as compared to the REALSTAR® Zika virus assay (Altona Diagnostics, Hamburg, Germany) and the APTIMA® Zika virus assay (Hologic Inc., Marlborough, Mass.).

The ZIKV assay was evaluated by testing 36 patient-matched serum, plasma, and urine specimens, and 25 whole blood specimens collected from endemic populations. Replicates of the serum samples were also evaluated with the REALSTAR® and APTIMA® assays, and replicates of the urine samples were evaluated with the REALSTAR® assay.

Using the automated Abbott m2000sp instrument together with the mSample RNA Preparation System kit (Abbott Molecular Inc, Des Plaines, Ill.), Zika virus RNA was extracted from 0.5 mL of sample, and 40 μl from each purified RNA sample was combined with an equal volume of activated mastermix solution in a well on a plate. Zika virus RNA was detected using the primer and probe sequences directed to the prM and NS3 coding regions described herein. The thermal cycling conditions consisted of 1 cycle of a denaturing step (60° C. for 30 minutes), and 45 cycles of an amplification step (92° C. for 20 seconds, then 55° C. for 45 seconds). Both of the prM and NS3 targets were detected in the same fluorescent channel (FAM). Each assay additionally included inactivated Zika virus strain PRVABC59 (Zeptometrix, Buffalo, N.Y.) diluted in purified protein matrix as a positive control to ensure that the RNA extraction method was consistent between runs, and normal human plasma that is negative for HIV-1/2, HBV, and HCV as a negative control to confirm that no contaminating Zika virus RNA was detected. The two probes specific for the Zika virus targets (prM and NS3) were labeled with the same fluorophore (FAM), while the positive control was labeled with a different fluorophore, allowing for simultaneous detection of both the Zika virus targets and the positive control in the same sample.

Zika virus RNA was detected in 29 out of 30 plasma samples and the patient-matched serum specimens with the ZIKV assay (see Table 7). The negative serum specimen that matched the negative plasma specimen had a CN value indicating a viral titer below the limit of detection (shaded box). Four specimens tested positive in plasma yet negative in serum, with plasma CN values indicating concentrations near or below the limit of detection. Zika virus was detected at similar levels in matched specimens.

Zika virus RNA was detected in 28 out of 29 serum specimens that also tested positive by the REALSTAR® assay (see Table 7). Two serum specimens tested positive by the ZIKV assay that were negative by the REALSTAR® assay. These specimens had CN values (underlined) that indicated the concentrations were near or below the limit of detection.

TABLE 7

| Plasma v. Serum Samples | | | |
|---|---|---|---|
| | | ZIKV assay Serum | |
| | | Positive | Negative |
| ZIKV assay Plasma | Positive | 29 | 4 |
| | Negative | 1 | 2 |
| | Total | 30 | 6 |
| Serum Samples | | | |
| | | REALSTAR ® Result | |
| | | Positive | Negative |
| ZIKV assay Result | Positive | 28 | 2 |
| | Negative | 1 | 5 |
| | Total | 29 | 7 |
| Urine Samples | | | |
| | | REALSTAR ® Result | |
| | | Positive | Negative |
| ZIKV assay Result | Positive | 21 | 2 |
| | Negative | 8 | 5 |
| | Total | 29 | 7 |

TABLE 7-continued

| Whole Blood v. Serum Sample | | | |
|---|---|---|---|
| | | APTIMA ® Serum Result | |
| | | Positive | Negative |
| ZIKV assay Whole Blood Result | Positive | 23 | 0 |
| | Negative | 2 | 0 |
| | Total | 25 | 0 |

The virus was detected in 21 out of the 29 urine specimens in the ZIKV assay that tested positive by the REALSTAR® assay (see Table 7). Seven of the eight urine specimens with negative results in the ZIKV assay had positive serum results in the ZIKV assay. Additionally, there were two specimens that tested positive by the ZIKV assay that were negative by the REALSTAR® assay; these had CN values indicating concentrations near or below the limit of detection.

All but 2 of the 25 whole blood specimens tested positive by the ZIKV assay (see Table 7). The first of these was invalid due to an internal control failure. Dilution of this specimen with an equal volume of negative plasma resulted in a valid, negative result. The second of these was positive on a re-test with a CN of 38.99, indicating a viral titer near or below the limit of detection.

The results of this example demonstrate the sensitivity of the Zika virus detection method described herein for a variety of different sample types.

All references, including publications, patent applications, and patents, cited herein, are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The present disclosure also contemplates other embodiments "comprising," "consisting of," and "consisting essentially of," the embodiments or elements presented herein, whether explicitly set forth or not. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition for amplifying and detecting a Zika virus nucleic acid sequence, which comprises a forward oligonucleotide primer, a reverse oligonucleotide primer, and an oligonucleotide probe, wherein the forward oligonucleotide primer comprises the nucleic acid sequence of SEQ ID NO: 1, the reverse oligonucleotide primer comprises the nucleic acid sequence of SEQ ID NO: 3, and the oligonucleotide probe comprises the nucleic acid sequence of SEQ ID NO: 5 and a detectable label.

2. The composition of claim 1, wherein the Zika virus nucleic acid sequence comprises a portion of a nucleic acid sequence that encodes a Zika virus prM protein.

3. The composition of claim 2, wherein the Zika virus nucleic acid sequence comprises the nucleic acid sequence of SEQ ID NO: 21.

4. The composition of claim 1, wherein the Zika virus is of the African lineage.

5. The composition of claim 1, wherein the Zika virus is of the Asian lineage.

6. A kit for amplifying and detecting a Zika virus nucleic acid sequence, which comprises:
   (a) a forward oligonucleotide primer comprising the nucleic acid sequence of SEQ ID NO: 1,
   (b) a reverse oligonucleotide primer comprising the nucleic acid sequence of SEQ ID NO: 3,
   (c) an oligonucleotide probe comprising the nucleic acid sequence of SEQ ID NO: 5 and a detectable label, and
   (d) reagents and instructions for amplifying and detecting a Zika virus nucleic acid sequence.

7. The kit of claim 6, wherein the Zika virus nucleic acid sequence comprises a portion of a nucleic acid sequence that encodes Zika virus prM protein.

8. The kit of claim 7, wherein the Zika virus nucleic acid sequence comprises the nucleic acid sequence of SEQ ID NO: 21.

9. The kit of claim 6, wherein the Zika virus is of the African lineage.

10. The kit of claim 6, wherein the Zika virus is of the Asian lineage.

* * * * *